United States Patent [19]
Yui et al.

[11] Patent Number: 5,747,016
[45] Date of Patent: May 5, 1998

[54] ORGANOPOLYSILOXANES AND A METHOD OF SETTING HAIR USING THE SAME

[75] Inventors: Koji Yui, Wakayama; Mari Takeshige, Funabashi; Takashi Oda; Akira Yoshimatsu, both of Wakayama; Takashi Itou, Ichikawa; Nakako Sato, Tokyo; Naohisa Kure, Tokyo, all of Japan

[73] Assignee: Kao Corporation, Tokyo, Japan

[21] Appl. No.: 763,344

[22] Filed: Dec. 11, 1996

Related U.S. Application Data

[63] Continuation of Ser. No. 288,394, Aug. 10, 1994, abandoned.

[30] Foreign Application Priority Data

| Aug. 10, 1993 | [JP] | Japan | 5-198657 |
| Aug. 11, 1993 | [JP] | Japan | 5-199361 |
| Sep. 1, 1993 | [JP] | Japan | 5-217722 |

[51] Int. Cl.$^6$ ............................ A61K 7/06; A61K 7/11
[52] U.S. Cl. ............... 424/401; 424/703.2; 424/DIG. 2; 424/78.02
[58] Field of Search ................ 424/DIG. 2, 70.12, 424/70.122, 70.11, 78.02

[56] References Cited

U.S. PATENT DOCUMENTS

| 4,344,763 | 8/1982 | Toigyesi | 8/127.51 |
| 4,559,227 | 12/1985 | Chandra | 424/70.122 |
| 4,563,347 | 1/1986 | Starch | 424/70.122 |
| 4,764,363 | 8/1988 | Bolich, Jr. | 424/47 |
| 5,089,253 | 2/1992 | Halloran | 424/47 |
| 5,180,580 | 1/1993 | Halloran | 424/71 |
| 5,220,033 | 6/1993 | Kamei | 548/406 |

FOREIGN PATENT DOCUMENTS

| 0 166 122 | 1/1986 | European Pat. Off. |
| 0 417 586 | 3/1991 | European Pat. Off. |
| 62-68820 | 3/1987 | Japan |
| 63-2918 | 1/1988 | Japan |
| 2-276824 | 11/1990 | Japan |
| 4-85334 | 3/1992 | Japan |
| 4-261113 | 9/1992 | Japan |
| 1 097 453 | 1/1968 | United Kingdom |

*Primary Examiner*—Sally Gardner-Lane
*Attorney, Agent, or Firm*—Oblon, Spivak, McClelland, Maier & Neustadt, P.C.

[57] ABSTRACT

An organopolysiloxane which generates intramolecular or intermolecular cross-linking based on dipole-dipole interaction, hydrogen bonding or ion bonding, and which is not ruptured or plastically deformed at an extension ratio no more than 15% at a temperature of 20° C. under relative humidity of 65%; and a method of setting hair using the same. Hair which is set by the method retains the given shape over time, and the organoplysiloxane imparts a soft touch to the hair. In addition, the shape given by the setting treatment can be easily restored to the original shape by ordinary shampooing.

3 Claims, No Drawings

ORGANOPOLYSILOXANES AND A METHOD OF SETTING HAIR USING THE SAME

This application is a Continuation of application Ser. No. 08/288,394, filed on Aug. 10, 1994, now abandoned.

BACKGROUND OF THE INVENTION

1. Field of the Invention

The present invention relates to novel organopolysiloxanes and to a method of setting hair using the same. More particularly, the invention relates to organopolysiloxanes which are excellent in the hair setting performance and the hair set retentivity, which provide soft touch to the set hair, which have good removal-by-shampoo property, and which are useful as an effective component in hair setting compositions, and to a method of setting hair using the same.

2. Description of Related Art

People make their hair styles in different manners. Generally, hair styles are made by applying a hair setting agent to dry or towel-dried hair, then giving hair a desired form with or without drying the hair naturally or with a drier. Hair setting agents which are generally used in this method are in the forms of foam, spray, mist, lotion, cream, gel, etc. Another method of making a hair style is to apply a hair setting agent in a spray or mist form to the hair which has been given shape by curlers and the like, and to maintain the given shape. In both methods, hair setting agents are required to have a function that maintains the finished hair style over time. In addition, good sensation free from roughness and stickiness is desirable.

Conventional hair setting agents generally contain film-forming setting polymers, examples of which include polyvinylpyrrolidones, vinylpyrrolidone-vinyl acetate copolymers, acrylic ester-methacrylic ester-acrylic acid copolymers, methylvinyl ether-maleic anhydride copolymers and copolymers of methacrylic esters (compounds in which dialkylaminoethyl methacrylate and monochloroacetic acid are bonded to each other).

Hair setting agents containing these film-forming setting polymers have a drawback that the formed hair style collapses as time passes. Especially, when the humidity is high, the shape of the set hair is easily lost.

The main reason which explains the lost of shape is that the setting polymer which is bonded to hair fibers is deformed over time. In highly humid conditions, the polymer plasticizes by absorbing humidity and thus easily gets deformed to shorten the set retention.

Therefore, setting polymers having high elasticity have been conventionally used to avoid easy deformation. However, such polymers involve a drawback in that the hair treated with them results in a stiff and rough texture, which is undesirable. In order to improve the touch to the hair, hair setting agents generally contain a variety of sensation improvers such as silicone oils, modified silicones and oil agents, which in turn deteriorate the set retaining ability. Accordingly, there has been a difficulty in obtaining a good set retention and favorable touch to the hair at the same time.

The shape of set hair also is lost by external force, such as winds and hand touch. Generally speaking, polymers having a high elasticity is brittle, so impacts of external force easily break polymer films before they get deformed, which causes collapsing of the set shape.

In order to overcome these problems, polymers which exhibit flexible and rubber-elastic properties without causing plastic deformation are required. Polymers which are free from plastic deformation include those having a intramolecular/intermolecular cross-linking such as in vulcanized rubbers. Cross-linked polymers are not suitable for the practical use because they generally have an extremely low solubility in solvents such as water and alcohols. Japanese Patent Application Laid-open (kokai) No. 4-139116 discloses a hair setting agent containing a polymer which is obtained by allowing a polyalkylene oxide and polycarboxylic acid or diisocyanate to react each other. This polymer forms a flexible film but is inferior to silicone derivatives with regard to the smoothness of the hair fibers.

In an attempt to impart favorable touch to hair fibers, silicone derivatives have been incorporated in hair cosmetic compositions. For example, Japanese Patent Application Laid-open (kokai) No. 61-158914 and Japanese Patent Application Laid-open (kokai) No. 61-161214 disclose hair cosmetic compositions which contain partially cross-linked organic silicone resins. These resins, however, are cross-linked by covalent bonds, which render the resulting compositions to have a very low solubility and poor removal-by-shampoo property which mar the appearance of the hair.

Japanese Patent Application Laid-open (kokai) No. 4-261113 discloses a composition for protecting the hair which contains a silicone polymer having a cross-linkable functional group, and a cross linking agent. A characteristic feature of this composition is that when the composition is exposed to the air, cross-linking takes place to exhibit properties like an elastomer. In order to give set retention property to a hair cosmetic composition, a certain extent of cross-linked structure must be present therein. But in the case of the composition according to this publication, if the degree of cross-linking is elevated to such an extent that set-retention property is evident, removal-by-shampoo property in turn deteriorates, that is, the composition cannot completely be removed by shampooing, which means that the hair style cannot be easily altered. This is because the cross-linking is based on covalent bonding.

Japanese Patent Application Laid-open (kokai) No. 63-2918 discloses a hair styling mousse which contains a hydroxylated polyorganosiloxane emulsion capable of forming an elastomer. The silicone elastomer disclosed in this publication is similar to that disclosed in U.S. Pat. No. 4,221,688, and forms an elastomer by cross-linking based on covalent bonding as in the above-mentioned Japanese Patent Application Laid-open (kokai) No. 4-261113. Accordingly, the elastomer involves the same disadvantage as mentioned above.

Japanese Patent Application Laid-open (kokai) No. 63-22010 discloses a hair styling composition which contains a hard type silicone polymer and a volatile carrier therefor. Examples of the polymer include, for example, filler reinforcing polydimethylpolysiloxane gums which encompass those having a terminal hydroxyl group, cross-linked siloxanes such as organic substituted silicone elastomers, organic substituted siloxane gums which encompass those having a terminal hydroxyl group, resin-reinforced siloxanes and cross-linked siloxane polymers.

However, organopolysiloxanes which are characterized only by a high molecular weight, or which merely contain a filler are vulnerable to plastic deformation and do not have good setting performance. Those which have a terminal hydroxyl group and which are cross-linked with fillers have an irreversible property. That is, if cross-linking proceeds until the setting property is evident, solubility and removal-by-shampoo property after application are extremely lowered. The organic substituted silicone elastomers are, like those described in the afore-mentioned Japanese Patent Application Laid-open (kokai) No. 63-2918, similar to those disclosed in U.S. Pat. No. 4,221,688, and involve the same disadvantage as mentioned above.

Moreover, Japanese Patent Application Laid-open (kokai) No. 60-68820, Japanese Patent Application Laid-open (kokai) No. 2-276824 and Japanese Patent Application Laid-open (kokai) No. 4-85334 disclose silicones which have been modified with a saccharide residue or poly(N-acylalkyleneimine). The silicones disclosed in these publications are low molecular weight silicones, and therefore, they are either liquid at room temperature or brittle even when they are solid. Thus, they are not suitable as components of hair setting compositions.

Japanese Patent Publication (Kokoku) No. 60-240732 disclose silicones which have been modified with betaine groups. The silicones disclosed in the publication are low molecular weight silicones and therefore, they are liquid at room temperature. Thus, they are not suitable as components of hair setting compositions.

In view of the foregoing, the present invention is to provide a method of setting hair in which excellent hair setting effect and prolonged set retention can be obtained, favorable soft touch is imparted to the hair after it has undergone a setting treatment, and the shape given by the setting treatment can be easily restored to the original shape by ordinary shampooing, and also to provide a novel organopolysiloxane which is used in this method.

SUMMARY OF THE INVENTION

Applicants have disclosed that organopolysiloxanes having specifically defined properties exhibit excellent hair-set retentivity, impart soft sensation to the hair, and are easily removed by shampooing.

Accordingly, an object of the present invention is to provide an organopolysiloxane which generates intramolecular or intermolecular cross-linking based on dipole-dipole interaction, hydrogen-bonding or ion bonding, and which is not ruptured or plastically deformed at an extension ratio no more than 15% at a temperature of 20° C. under relative humidity of 65%.

Another object of the present invention is to provide a method of setting hair by applying a composition which comprises the organopolysiloxane to the hair and then removing a solvent present in the composition.

A further object of the present invention is to provide a hair setting composition which contains the defined organopolysiloxane.

A still further object of the present invention is to provide for a use of the organopolysiloxane in setting hair.

The hair which is set by the method or the composition according to the present invention retains the given shape over time, and imparts a soft touch to the hair without roughening the hair. In addition, the shape given by the setting treatment can be easily restored to the original shape by ordinary shampooing.

The above and other objects, features and advantages of the present invention will become apparent from the following description.

DETAILED DESCRIPTION OF THE INVENTION AND PREFERRED EMBODIMENTS

The organopolysiloxane according to the present invention undergoes intramolecular and intermolecular cross-linking based on a bonding mechanism other than the covalent bonding. This phenomenon takes place in a solvent-free system or in a solution system of high concentration. Since the cross-linking is on a non-covalent bond basis, it is easily cleaved in a dilute solution. The presence of this cross-linking can be confirmed under transmission electron microscope (TEM) to check whether a micro phase separation is observed.

The organopolysiloxane according to the present invention is preferably in a solid state at normal ambient temperatures and under normal pressure (Generally, −10° to 40° C., 1 atm). Moreover, the organopolysiloxane is preferably soluble or completely dispersible in water or in lower alcohols, so that the cross-linking is easily cleaved in water or in lower alcohols. The lower alcohols are preferably C1 to C6 alcohols.

The bonding mechanism according to the present invention is dipole-dipole interaction, hydrogen bonding or ion bonding and must be easily cleaved in water or lower alcohols. The organopolysiloxane according to the present invention has one or more functional groups which permits formation of the above bonds.

The organopolysiloxane according to the present invention is not ruptured or plastically deformed at an extension ratio no more than 15% at 20° C. under relative humidity of 65%. Generally speaking, deformed polymers can easily restore their original shape if the deformation degree is small, but when the deformation degree is significant, they do not. This phenomenon in which the original shape is not recovered is called plastic deformation. If a polymer is hard and brittle, it may rupture before plastic deformation takes place. In either case of rupture or plastic deformation, the original shape cannot be restored, and therefore, polymers which cause them are not suitable as hair setting polymers. Accordingly, the above-mentioned property possessed by the organopolysiloxane according to the present invention is a so-called rubber-elasticity, and it is a very important property for imparting a strong set retentivity and improving the touch to the hair which has undergone a setting treatment.

Whether plastic deformation takes place or not in no more than 15% extension can be confirmed by a simple test. A test piece having a thickness of about 0.2 mm, a length of about 20 mm and a width of about 5 mm is extended by 3 mm (15%) at a crosshead speed of 20 mm/min while the stress-strain curve is recorded at a temperature of 20° C. and under relative humidity of 65%. Immediately thereafter, the crosshead is returned to the original position at the same speed. After 10 minutes, the test piece is extended again. If the stress-strain curve recorded in the second test is identical to the curve recorded in the first test, the test piece is completely restored without causing any plastic deformation. By contrast, if plastic deformation takes place, the test piece has been lengthened after the reciprocating movement in the first test, the stress is imposed on the test piece with a time lag in the second test, and as a result, the stress-strain curve becomes different from the curve in the first test.

No particular limitation is imposed on the organopolysiloxanes as long as they undergo intramolecular and intermolecular cross-linkings based on dipole-dipole interaction, hydrogen bonding or ion bonding, and are not broken or plastically deformed at an extension ratio no more than 15% at 20° C. under relative humidity of 65%. However, in order to generate intramolecular and intermolecular cross-linkings based on dipole-dipole interaction, hydrogen bonding or ion bonding, a polar functional group must be present in a side chain or at a terminal of an organopolysiloxane segment. Examples of such polar functional group include a group having dipole-dipole interaction, a group having hydrogen bonds, and a group having ionic bonds. Examples of the group having dipole-dipole interaction include N-acylalkyleneimine and pyrrolidon. Examples of the group having hydrogen bonds include: a group having hydroxide group, such as a sugar and polyvinylalcohol; a group having amide groups, such as, poly-N-morpholin(meth)acrylamide, poly-N-vinylvinylpyrrolidone, poly-N-vinylacetoamide, polyaminoacid, and $C_{1-4}$ mono- or di-alkyl(meth)acrylamide polymer including poly(meth)acrylamide, polydimethylacrylamide and polydiethylacrylamide. Examples of the group having ionic bonds include an amphoteric ionomer and an amineoxide. The amphoteric ionomer is for example a betaine polymer such as carbobetaine, sulfobetaine and phosphobetaine; a copolymer of an anionic monomer such as acryl acid, and a cationic monomer such N,N-dimetylaminoethyl(meth)acrylate and N,N-dimethylaminopropyl(meth)acrylamide.

Examples of the organopolysiloxanes according to the present invention include the following (A), (B), (C) and (D).

(A): Organopolysiloxanes in which at least one silicon atom in a side chain or at a terminal of an organopolysiloxane segment is bonded, through an alkylene group having a hetero atom, to poly(N-acylalkyleneimine) constituted by a recurring unit represented by the following general formula (1):

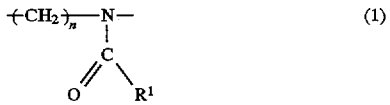

wherein $R^1$ represents hydrogen, C1–C22 alkyl, cycloalkyl, aralkyl or aryl, and n represents a number of 2 or 3.

In these organopolysiloxanes (A), the ratio by weight between the organopolysiloxane segment and the poly(N-acylalkyleneimine) segment is from 98/2 to 40/60. More preferably, the ratio is from 94/6 to 60/40 and the weight-average molecular weight of the organopolysiloxane is from 50,000 to 500,000, more preferably from 100,000 to 300,000. If the ratio by weight between an organopolysiloxane segment and a poly(N-acylalkyleneimine) segment is over 98/2 or under 40/60, or the weight average molecular weight of the organopolysiloxane is less than 50,000, rupture or plastic deformation tend to occur before the extension ratio reaches 15%. On the other hand, if the weight average molecular weight exceeds 500,000, production of organopolysiloxane becomes difficult.

Examples of the alkylene group which has a hetero atom and which is present between an organopolysiloxane segment and a poly(N-acylalkyleneimine) segment for bonding them include a C2–C20 alkylene which contains 1 to 3 nitrogen atoms, oxygen atoms and/or sulfur atoms. Specific examples include the following:

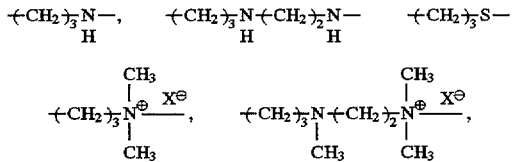

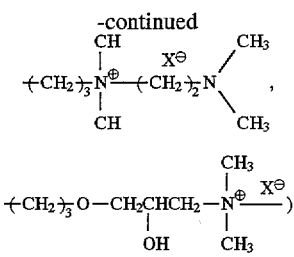

wherein $X^-$ represents a counter ion of a quaternary ammonium salt.

In the organopolysiloxanes (A), the cycloalkyl group represented by $R^1$ are those having 3 to 6 carbon atoms. Examples of the aralkyl group include phenylalkyl and naphthylalkyl. Examples of aryl group include phenyl, naphthyl and alkyl-substituted phenyl.

The organopolysiloxanes (A) are prepared by allowing the organopolysiloxane represented by the following formula (2):

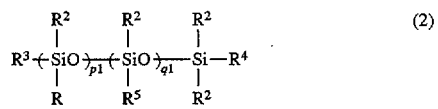

wherein the substituents $R^2$ are the same or different from each other and independently represent C1–C22 saturated alkyl or phenyl; $R^3$ and $R^{4,}$ independently, are the same as $R^2$ or, independently represent the following groups:

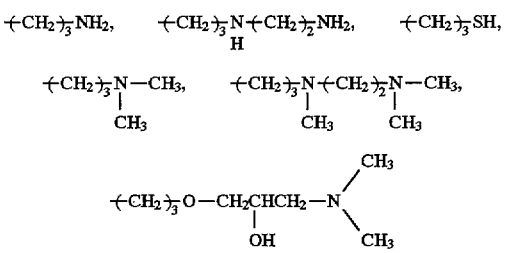

$R^5$ represents the following groups,

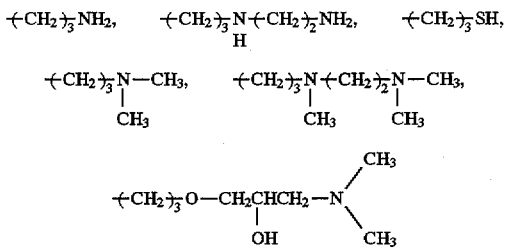

$p^1$ represents an integer of 100 to 400 and $q^1$ represents an integer of 1 to 300, to react with a terminal reactive poly(N-acylalkyleneimine) obtained by a ring-opening polymerization of a cyclic iminoether represented by the following formula (3):

wherein n represents a number of 2 or 3 and $R^1$ has the same meaning as above.

The ring-opening polymerization of the cyclic iminoether (3) is carried out by the use of compounds having strong electrophilic reactivity, such as methyl, ethyl, 3-propenyl or benzyl esters of strong acids, for example, benzenesulfonic acid, p-toluenesulfonic acid, trifluoromethane sulfonic acid, trifluoroacetic acid, or sulfuric acid as an initiator. If 2-substituted-2-oxazoline is used for the cyclic iminoether (3), poly(N-acylethyleneimine) (compound of formula (1), in which n=2) is obtained. Alternatively, if 2-substituted-2-oxazine is used, poly(N-acylpropyleneimine) (compound of formula (1), in which n=3) is obtained.

In order to link the above-mentioned poly(N-acylethyleneimine) chain to a silicone chain, a variety of reactions may be employed, which include an ester forming reaction based on the condensation between a carboxyl group and a hydroxyl group; an amide forming reaction based on the condensation of a carboxyl group and an amino group; a secondary, tertiary or quaternary ammonium forming reaction between a halogenized alkyl group and a primary, secondary or tertiary amino group; and a beta-hydroxylamine forming reaction utilizing an epoxy group and an amino group. Japanese Patent Application Laid-open (kokai) 2-276824, Japanese Patent Application Laid-open (kokai) 4-85334, Japanese Patent Application Laid-open (kokai) 4-85335, Japanese Patent Application Laid-open (kokai) 4-96933, for instance, describe a method in which a terminal reactive poly(N-acylalkyleneimine) obtained by a cationic ring-opening polymerization of a cyclic iminoether reacts with an organopolysiloxane represented by formula (2), i.e., a modified organopolysiloxane having side chains substituted by the aforementioned groups. This method is advisable in view of its simplicity and efficiency.

(B): Organopolysiloxanes in which at least one silicon atom in a side chain or at a terminal of an organopolysiloxane segment is bonded to the group represented by the following formula (4): wherein m represents a number of 1 to 8.

In these organopolysiloxanes (B), the number of the silicon atoms bonded to the group represented by formula (4) occupies 10 to 90%, preferably 40 to 80%, of the total number of the silicon atoms in the molecule. The weight-average molecular weight is preferably from 50,000 to 300,000, and more preferably from 100,000 to 200,000. If the weight-average molecular weight of the organopolysiloxanes (B) is less than 50,000, rupture or plastic deformation tend to occur before the extension ratio reaches 15%. On the other hand, if the weight-average molecular weight exceeds 300,000, production of organopolysiloxanes becomes difficult. If the number of the silicon atoms bonded to the group represented by formula (4) occupies less than 10%, sufficient cross-linking cannot occur, and therefore, the organopolysiloxanes (B) tend to rupture or deform before the extension ratio reaches 15%. On the other hand, if the number exceeds 90%, favorable sensation which is a characteristic feature of silicones is not obtained to any significant degree.

In order to obtain organopolysiloxanes (B), a so-called hydrosilyl reaction may be used, in which an organohydrogenpolysiloxane represented by the formula (5) below is used as a precursor and is allowed to react with N-alkylenepyrrolidone. This hydrosilyl reaction is carried out in a solvent of a halogen series such as dichloromethane, chloroform, or 1,2-dichloroethane, or in an aliphatic ether such as tetrahydrofuran, diisopropylether or dibutylether at a temperature between room temperature and 100° C. using a transition metal complex such as platinum chloride as a catalyst.

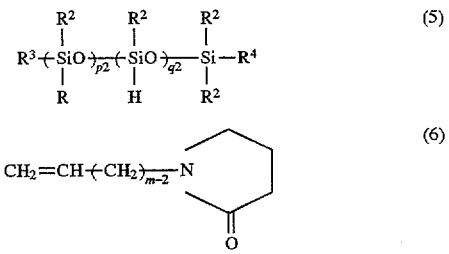

wherein $p^2$ represents an integer of 30 to 3,000, $q^2$ represents an integer of 60 to 1,500, and $R^2$, $R^3$, $R^4$ and m have the same meaning as defined above.

Japanese Patent Application Laid-open (kokai) 5-32784 discloses compounds which are analogous to the above-described organopolysiloxanes (B) as well as methods of preparing them. However, this publication is silent on the molecular weight of the disclosed organopolysiloxane compounds. Moreover, the elastomeric property in which rupture or deformation are not caused until the extension ratio reaches 15% is not disclosed at all. Furthermore, examples of this publication only contain such compounds which rupture or deform before the extension ratio reaches 15% are illustrated.

(C): Organopolysiloxanes in which at least one silicon atom in a side chain or at a terminal of an organopolysiloxane segment is bonded to a saccharide residue.

In these organopolysiloxanes (C), examples of the saccharide residue include a sugar lactone amidealkyl group (a group composed of a sugar lactone compound and an aminoalkyl group bonded thereto by an amide bond). The organopolysiloxanes (C) preferably have 40 to 97% by weight, more preferably 50 to 85% by weight, of silicone chains. The weight-average molecular weight of the organopolysiloxanes (C) preferably ranges from 50,000 to 500,000, and more preferably from 100,000 to 300,000. If the proportion of the silicone chains is less than 40% by weight, rupture or plastic deformation tend to occur before the extension ratio reaches 15%, and thus rubber-elasticity is not obtained to any significant degree. On the other hand, if the proportion exceeds 97% by weight, cross-linking is insufficient, thereby resulting in a paste like material. The rubber-elasticity also is not obtained in this case. If the weight-average molecular weight of the organopolysiloxanes (C) is less than 50,000, rupture or plastic deformation t end to occur before the extension ratio reaches 15%, and if it exceeds 500,000, production of organopolysiloxanes becomes difficult.

In order to obtain the organopolysiloxanes (C), an organopolysiloxane having at least one aminoalkyl group is allowed to react with a sugar lactone compound (a compound which is obtained by subjecting aldonic acid or uronic acid to an intramolecular cyclodehydration) to generate amide bonds.

The aminoalkyl groups are those having 1 to 20, more preferably 1 to 8, carbon atoms. Examples of the lactone compounds which are obtained from the intramolecular cyclodehydration of aldonic acid or uronic acid include lactones of aldonic acid derived from a reducing monosaccharide such as D-glucose, D-galactose D-allose, D-aldose, D-mannose, D-gulose, D-idose, and D-talose; lactones of aldonic acid derived from a reducing disaccharide such as maltose, cellobiose, lactose, xylobiose, isomaltose, nigerose, and kojibiose; lactones of aldonic acid derived from a reducing trisaccharide such as maltotriose, banose, panose, and isomaltotriose; lactones of aldonic acid derived from a reducing oligosaccharide containing more than four simple sugars; and lactones of an uronic acid such as D-glucuronic acid, L-iduronic acid and mannuronic aid. These are used singly or in combination.

The reaction between an organopolysiloxane precursor having an aminoalkyl group and a sugar lactone is carried out using, preferably, 1.0 to 1.3 mol fold of a sugar lactone based on the amino group of an organopolysiloxane precursor. The precursor and the sugar lactone are mixed in a solvent, and then stirred for 3 to 20 hours while refluxing with heat at the solution concentration of 5 to 30% by weight. Suitable solvents in this step are lower alcohols such as methanol, ethanol, 1-propanol and 2-propanol.

(D): Organopolysiloxanes in which at least one silicon atom in a side chain or at a terminal of an organopolysiloxane segment is bonded, through an alkylene group containing a hetero atom, to a poly(N-propylene carbobetaine) segment containing a recurring unit represented by the following formula (7):

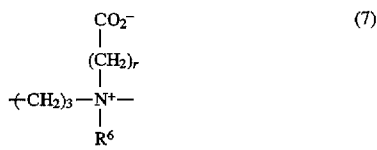

wherein $R^6$ represents hydrogen, C1–C22 alkyl, cycloalkyl, aralkyl, aryl or alkoxycarbonylalkyl, and r represents a number from 1 to 5.

These organopolysiloxanes (D) preferably have a ratio by weight of the organopolysiloxane segment and the poly(N-propylene carbobetaine) segment of from 98/2 to 40/60 (more preferably from 90/10 to 60/40), and a weight-average molecular weight of from 50,000 to 500,000 (more preferably from 100,000 to 300,000). If the ratio by weight of the organopolysiloxane segment and the poly(N-propylene carbobetaine) segment exceeds 98/2 or below 40/60, or the weight-average molecular weight is less than 50,000, rupture or plastic deformation tend to occur before the extension ratio reaches 15%. On the other hand, if the weight-average molecular weight exceeds 500,000, production of organopolysiloxanes becomes difficult.

Examples of the alkylene group containing a hetero atom which intervenes in the linkage of an organopolysiloxane segment and a poly(N-propylene carbobetaine) segment include a C2–C20 alkylene group containing 1 to 3 nitrogen atoms, oxygen atoms, and/or sulfur atoms. More specifically, the compounds which are represented by the following formulae may be mentioned:

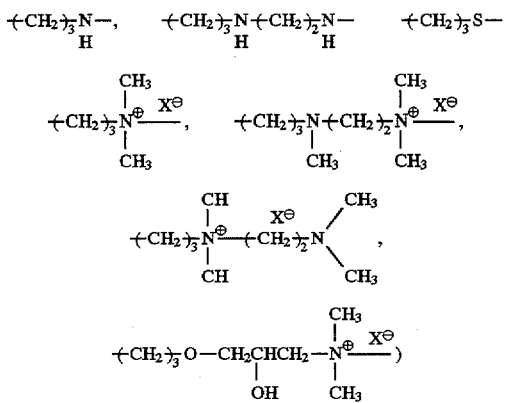

wherein X– is a counter ion of a quaternary ammonium salt. Among the groups represented by $R^6$, the cycloalkyl group has 3 to 6 carbon atoms, the aralkyl group includes phenylalkyl, naphthylalkyl, etc.; and the aryl group includes phenyl, naphthyl and alkyl-substituted phenyl.

The above-described organopolysiloxanes (D) are prepared as follows. First, an organopolysiloxane of formula (2) is allowed to react with terminal reactive poly(N-propyleneimine) obtained by a ring-opening polymerization of a cyclic amine represented by the following formula (8):

wherein $R^6$ has the same meaning as described above, to prepare an organopolysiloxane to which poly(N-propylene imine) is bonded. Then, the obtained product is allowed to react with sodium chloroacetate, β-propiolactone, γ-butyrolactone, ε-caprolactone to obtain organopolysiloxanes (D) which contain a poly(N-propylene carbobetaine) segment.

Alternatively, the organopolysiloxanes (D) may be prepared by quaternarizing, by the use of a C1–C22 alkyl halide, cycloalkyl halide or an aryl halide, an organopolysiloxane to which a poly(N-propylene imine) segment is bonded, and subsequently bringing the alkoxycarbanylethyl or alkoxycarbonylmethyl group to a hydrolizing reaction under basic conditions.

The ring-opening polymerization of a cyclic amine is performed using, as a polymerization initiator, Lewis acid, protonic acid, or alkylating agents such as triethyloxonium tetrafluoroborate, benzyl chloride, benzyl bromide, benzyl iodide, methyl bromide, methyl iodide, ethyl bromide, ethyl iodide, dimethyl sulfate, diethyl sulfate, trifluoromethane sulfonic acid, methyl trifluoromethane sulfonate, ethyl trifluoromethane sulfonate, benzene sulfonic acid, methyl benzene sulfonate, ethyl benzene sulfonate, p-toluenesulfonic acid, methyl p-toluenesulfonate, and ethyl p-toluenesulfonate.

If N-substituted azetidine is used as a cyclic amine, poly(N-substituted propylene carbobetaine) is obtained.

Examples of a solvent which may be used in the ring-opening polymerization of a cyclic amine or in the manufacture of the copolymers of the present invention include acetic esters such as ethyl acetate and propyl acetate; ethers such as diethylether, diisopropylether, dioxane and tetrahydrofuran; ketones such as acetone and methylethyl ketone; halogen solvents such as chloroform and methylene chloride; nitrile solvents such as acetonitrile and benzonitrile; and non-protonic polar solvents such as N,N-dimethylformamide, N,N-dimethylacetamide and dimethylsulfoxide.

The poly(N-propylene imine) chain is linked to a silicone chain in a similar manner that the above-mentioned poly(N-acylalkylene imine) chain is linked to a silicone chain.

In order to set hair fibers using the organopolysiloxane according to the present invention, a composition containing the organopolysiloxane is first applied to the hair fibers and then the solvent present in the composition is removed. It is preferred that the organopolysiloxane be incorporated in the composition in a proportion of 0.05 to 20% by weight, more preferably 0.1 to 10% by weight, of the composition.

The composition may further contain optional ingredients including solvents such as water and ethanol, and a variety of ingredients which are ordinarily incorporated in hair setting compositions such as surfactants, oils, polyols, medicinal ingredients, preservatives, perfumes, etc., according to the purpose, use, intended form of the composition, etc. Examples of the surfactants include linear or branched alkylbenzenesulfonates, ethylene oxide and/or propylene oxide-added alkyl- or alkenyl- ether sulfates, olefinsulfonates, alkanesulfonates, saturated or unsaturated fatty acid salts, ethylene oxide and/or propylene oxide-added alkyl- or alkenyl- ether carboxylates, esters of alpha-sulfofatty acid salts, amino acid-type surfactants, phosphate-type surfactants, sulfosuccinic acid-type surfactants, sulfonic acid-type amphoteric surfactants, betaine-type amphoteric surfactants, alkylene amine oxides, cationic surfactants such as linear and/or branched alkyl- or alkenyl- quaternary ammonium salts, polyoxyalkylene alkyl- or alkenyl- ethers, polyoxyalkylene alkylphenylethers, addition products of higher fatty acid alkanolamides or alkylene oxides, esters of polyols and fatty acids, esters of sorbitol and fatty acids, esters of sucrose and fatty acids, and esters of higher alcohols and saccharides. The amount of surfactants to be incorporated into the composition is preferably from 0 to 10% by weight, and particularly preferably from 0 to 5% by weight.

Examples of the oils include higher fatty acids such as stearic acid, higher alcohols such as cetanol, cholesterol, Vaseline, cholesteryl isostearate, solid fats such as sphingolipids, squalene, jojoba oil, other liquid fats of silicone derivatives, etc. Examples of the polyols include glycerol, 1,3-butylene glycol, propylene glycol, dipropylene glycol, polyethylene glycol, polyglycerol, sorbitol, etc. Examples of the solvents other than water and ethanol include benzyl alcohol, 2-benzyloxyethanol, N-alkylpyrrolidone, diethylene glycol monoethylether, etc. Other ingredients include pearl-hue imparting agents, perfumes, colorants, UV absorbers, antioxidants, bacteriostats such as triclosan and triclocarban, antiinflammatory agents such as potassium glycyrrhizate and tocopherol acetate, antidandruff agents such as zinc pyrithione and Octopirox, preservatives such as methylparaben and butylparaben, and pH modifiers such as lactic acid and citric acid. These optional ingredients may be arbitrarily incorporated into the compositions as long as the effects of the invention are not impeded.

In order to obtain more enhanced effects, i.e., strong setting power which effectively retains the hair style made by blow setting or combing even under highly humid conditions, and soft and smooth touch without inviting rough or sticky hair, it is preferred that dimethylpolysiloxane having a polymerization degree of not less than 5,000, preferably not less than 10,000, especially preferably not less than 15,000 be incorporated into the compositions.

The compositions can be processed into a variety of forms including sprays, mists, lotions, tonics, blows, creams, post-foaming gels, etc., according to conventional methods. When the compositions are prepared into aerosols, injection gases including volatile hydrocarbons such as butane, isobutane, pentane and isopentane; hydrocarbon halides such as dichlorofluoromethane and dichlorotetrafluoroethane; dimethylether; carbon dioxide; nitrogen; and air can be incorporated therein.

When a film-forming polymer is incorporated into the compositions, set retention power is even further enhanced, and excellent smooth touch to the hair is obtained.

Examples of the film-forming polymer include the following (1) to (8) compounds.

(1) Polymers of a polyvinylpyrrolidone series:
Polyvinylpyrrolidone
Luviskol K12, K30 (by BASF), PVP K15, K30 (by GAF), etc. are commercially obtainable.

Polyvinylpyrrolidone/vinyl acetate copolymers
Luviskol VA28, VA73 (by BASF), PVP/VA E-735, S-630 (by GAF), etc. are commercially obtainable.

Polyvinylpyrrolidone/vinyl acetate/vinyl propyonate ternary copolymers
Luviskol VAP343 (by BASF), etc. are commercially obtainable.

Polyvinylpyrrolidone/alkylamino acrylate copolymers
Luviflex (by BASF), Copolymer 845, 937 and 958 (by GAF), etc. are commercially obtainable.

Polyvinylpyrrolidone/acrylate/(meth)acrylic acid copolymers
Luviflex VBM35 (by BASF), etc. are commercially obtainable.

Polyvinylpyrrolidone/alkylamino acrylate/vinyl caprolactam copolymers
Copolymer VC-713 (by GAF), etc. are commercially obtainable.

(2) Polymers of an acidic vinyl ether series:
Methylvinyl ether/maleic anhydride alkyl half ester copolymers
Gantrez ES-225, ES-425, SP-215 (by GAF), etc. are commercially obtainable.

(3) Polymers of an acidic polyvinyl acetate series:
Vinyl acetate/crotonic acid copolymers
Resin 28-1310 (by National Starch), Luviset CA66 (by BASF), etc. are commercially obtainable.

Vinyl acetate/crotonic acid/vinyl neodecanoate copolymers
Resin 28-2930 (by National Starch), etc. are commercially obtainable.

Vinyl acetate/crotonic acid/vinyl propionate copolymers
Luviset CAP (by BASF), etc. are commercially obtainable.

(4) Polymers of an acidic acrylic series:
(Meth)acrylic acid/(meth)acrylic ester copolymers
Plascize L53P (by Goo Chemical), Diahold (by Mitsubishi Petrochemical), etc. are commercially obtainable.

Acrylic acid/acrylic acid alkyl ester/alkyl acrylamide copolymers
Ultrahold 8 (by BASF), Amphomer V-42 (by National Starch), etc. are commercially obtainable.

(5) Polymers of an amphoteric acrylic series:
(Meth)acrylethyl betaine/(meth)acrylic acid alkyl ester copolymers
Polymers of this type include copolymer of N-methacryloyloxyethyl-N,N-dimethylammonium-α-N-methylcarboxybetaine and alkyl (meth)acrylate, and commercial products include Yukaformer M-75, SM (by Mitsubishi Petrochemical).

Acrylic acid alkyl ester/butylaminoethyl methacrylate/octylamide acrylate copolymers
Polymers of this type include octylacrylamide/acrylate/butylaminoethyl methacrylate polymers, and commercial products include Unformer 28-4910 (by National Starch).

(6) Polymers of a basic acrylic series:
Acrylamide/acryl ester quaternary system copolymers
Polymers described in Japanese Patent Application Laid-open (kokai) 2-180911 are mentioned.

(7) Cellulose derivatives:
Cationic cellulose derivatives: Celquat H-100, L-200 (by National Starch), etc. are commercially obtainable.

(8) Chitin/chitosan derivatives:
Hydroxypropyl chitosan
Chitofilmer (by Ichimaru-Pharcos), etc. are commercially obtainable.

Carboxymethyl chitin, carboxymethyl chitosan, salts of chitosan and a monovalent acid such as pyrrolidone carboxylic acid, lactic acid, and glycolic acid, or of chitosan and a divalent acid such as adipic acid and succinic acid Chitomer PC (pyrrolidone carboxylic acid salt), Chitomer L (lactic acid salt), both by Union Carbide are commercially obtainable.

Among the above-described film-forming polymers, (math)acrylic polymers, amphoteric acrylic polymers, polyvinylpyrrolidone polymers, polymers having a sugar skeleton and salts of chitosan are especially preferred.

The amount of these film-forming polymers to be incorporated into the afore-mentioned compositions is preferably from 0.05 to 20%, and particularly preferably from 0.1 to 10% by weight.

The above-described compositions are applied to the hair in various manners according to the forms of the compositions. Generally, spraying, applications by hands and combinations of the them are employed. The removal of solvents is preferably performed by natural drying or drying with heat. When the hair fibers are set to have a desired shape, shape is preferably given after application and before drying. Generally, the hair is set by the use of a hair brush or curlers.

EXAMPLES

The present invention will further be described by way of examples, which should not be construed as limiting the invention thereto.

In the following examples, the % content of a silicone segment was obtained by quantitatively determining Si atoms by plasma emission analysis. The weight-average molecular weight in the examples is that of polystyrene equivalent calculated based on the results of gel permeation liquid chromatography using chloroform as a developer.

Synthesis Example 1

Organopolysiloxane A-1

Diethyl sulfate (21.4 g; 0.139 mol) and 2-ethyl-2-oxazoline (331 g; 3.33 mol) were dissolved in dehydrated ethyl acetate (700 g). The solution was refluxed with heat for 5 hours in the atmosphere of nitrogen to synthesize a terminal reactive poly(N-propionylethyleneimine). To this, side-chain primary aminopropyl-modified polydimethylsiloxane (molecular weight: 110,000, amine equivalent: 4840) (560 g; amino group equivalent=0.116 mol) in ethyl acetate (50% solution) was added at a time and refluxed with heat over 10 hours. The reaction mixture was condensed under reduced pressure. An N-propionylethyleneimine-dimethylsiloxane copolymer was obtained as a pale yellow rubber-like solid (885 g; yield=97%). The weight-average molecular weight was 109,000. When a neutralization titration was performed using HCl in methanol, no residual amino groups were found.

Comparative Synthesis Example 1

Organopolysiloxane a:

Diethyl sulfate (21.4 g; 0.139 mol) and 2-ethyl-2-oxazoline (331 g; 3.33 mol) were dissolved in dehydrated ethyl acetate (700 g). The solution was refluxed with heat for 5 hours in the atmosphere of nitrogen to synthesize a terminal reactive poly(N-propionylethyleneimine). To this, side-chain primary aminopropyl-modified polydimethylsiloxane (molecular weight: 24,000, amine equivalent: 4810) (560 g; amino group equivalent=0.116 mol) in ethyl acetate (50% solution) was added at a time and refluxed with heat over 10 hours. The reaction mixture was condensed under reduced pressure. A N-propionylethyleneimine-dimethylsiloxane copolymer was obtained as a pale yellow rubber-like solid (867 g; yield=95%). The weight-average molecular weight was 25,800. When a neutralization titration was performed using HCl in methanol, no residual amino groups were found.

Synthesis Example 2

Organopolysiloxane A-2:

Diethyl sulfate (30.6 g; 0.199 mol) and 2-ethyl-2-oxazoline (945 g; 9.53 mol) were dissolved in dehydrated ethyl acetate (1,950 g). The solution was refluxed with heat for 8 hours in an atmosphere of nitrogen to synthesize a terminal reactive poly(N-propionylethyleneimine). To this, a side-chain primary aminopropyl-modified polydimethylsiloxane (molecular weight: 110,000, amine equivalent: 4840) (800 g; amino group equivalent=0.165 mol) in ethyl acetate (50% solution) was added at a time and refluxed with heat over 12 hours. The reaction mixture was condensed under reduced pressure. A N-propionylethyleneimine-dimethylsiloxane copolymer was obtained as a pale yellow rubber-like solid (1,720g; yield=97%). The weight-average molecular weight was 122,000. When a neutralization titration was performed using HCl in methanol, no residual amino groups were found.

Synthesis Example 3

Organopolysiloxane A-3:

Diethyl sulfate (3.56 g; 0.0230 mol) and 2-ethyl-2-oxazoline (27.5 g; 0.277 mol) were dissolved in dehydrated ethyl acetate (60 g). The solution was refluxed with heat for 4 hours in an atmosphere of nitrogen to synthesize a terminal reactive poly(N-propionylethyleneimine). To this, side-chain primary aminopropyl-modified polydimethylsiloxane (molecular weight: 110,000, amine equivalent: 20800) (400 g; amino group equivalent=0.0192 mol) in ethyl acetate (50% solution) was added at a time and refluxed with heat over 8 hours. The reaction mixture was condensed under reduced pressure. A N-propionylethyleneimine-dimethylsiloxane copolymer was obtained as a pale yellow rubber-like solid (428 g; yield=99%). The weight-average molecular weight was 115,000. When a neutralization titration was performed using HCl in methanol, no residual amino groups were found.

Synthesis Example 4

Organopolysiloxane B-1:

2.0 g of a 5% isopropylalcohol solution of chloroplatinic acid was added to methylhydrogen polysiloxane (500 g; 2.91 mol as SiH; weight-average MW=100,000; SiH equivalent=172), and stirred in the atmosphere of nitrogen. N-(3-propenyl)pyrrolidone (382 g; 3.06 mol) was added dropwise to the mixture obtained at such a speed that the temperature of the reaction system did not exceed 60° C. After completion of the addition, the temperature of the system was maintained at 65° C., and the mixture was stirred for further 3 hours. Thereafter, the temperature was returned to room temperature. To this, ethanol (3530 g) was added to make a uniform solution. Activated carbon powder (10 g) was added to the uniform solution, and the solution was stirred for 30 minutes at room temperature. Subsequently, the activated carbon was removed by filtration. The solution so obtained was concentrated under reduced pressure. Ethanol and unreacted N-(3-propenyl)pyrrolidone were distilled off. Methylpolysiloxane (847 g; yield=98%) having an alkylpyrrolidone group as a side chain was obtained as a colorless transparent rubber-like solid. The weight-average molecular weight was 155,000. In the FT-IR spectrum, absorption of Si-H stretching vibration (2125 cm$^{-1}$) was not observed.

Comparative Synthesis Example 2:

Organopolysiloxane b:

2.0 g of a 5% isopropylalcohol solution of chloroplatinic acid was added to methylhydrogen polysiloxane (500 g; 2.97 mol as SiH; weight-average MW=4,300: SiH equivalent=168), and stirred in an atmosphere of nitrogen. N-(3-propenyl)pyrrolidone (390 g; 3.12 mol) was added dropwise to the obtained mixture at such a speed that the temperature of the reaction system did not exceed 60° C. After completion of the addition, the temperature of the system was maintained at 65° C., and the mixture was stirred for further 3 hours. Thereafter, the temperature was returned to room temperature. To this, ethanol (3600 g) was added to make a uniform solution. Activated carbon powder (10 g) was added to the uniform solution, and the solution was stirred for 30 minutes at room temperature. Subsequently, the activated carbon was removed by filtration. The solution so obtained was concentrated under reduced pressure. Ethanol and unreacted N-(3-propenyl)pyrrolidone were distilled off. Methylpolysiloxane (819 g; yield=94%) having an alkylpyrrolidone group as a side chain was obtained as a colorless transparent rubber-like solid. The weight-average molecular weight was 7,100. In the FT-IR spectrum, absorption of Si—H stretching vibration (2125 cm$^{-1}$) was not observed.

Synthesis Example 5

Organopolysiloxane A-4:

Diethyl sulfate (3.75 g; 0.0244 mol) and 2-ethyl-2-oxazoline (58.6 g; 0.591 mol) were dissolved in dehydrated ethyl acetate (125 g). The solution was refluxed with heat for 5 hours in an atmosphere of nitrogen to synthesize a terminal reactive poly(N-propionylethyleneimine). To this, a side-chain primary aminopropyl-modified polydimethylsiloxane (molecular weight: 110,000, amine equivalent: 9840) (200 g; amino group equivalent=0.0203 mol) in ethyl acetate (50% solution) was added at a time and refluxed with heat over 8 hours. The reaction mixture was condensed under reduced pressure. A N-propionylethyleneimine-dimethylsiloxane copolymer was obtained as a pale yellow rubber-like solid (257 g; yield=98%). The % content of silicone segments was 76%, and the weight-average molecular weight was 118,000. When a neutralization titration was performed using HCl in methanol, no residual amino groups were found.

Synthesis Example 6

Organopolysiloxane A-5:

Diethyl sulfate (29.7 g; 0.193 mol) and 2-ethyl-2-oxazoline (153 g; 1.54 mol) were dissolved in dehydrated ethyl acetate (370 g). The solution was refluxed with heat for 3 hours in the atmosphere of nitrogen to synthesize a terminal reactive poly(N-propionylethyleneimine). To this, side-chain primary aminopropyl-modified polydimethylsiloxane (molecular weight: 90,000, amine equivalent: 1870) (300 g; amino group equivalent=0.160 mol) in ethyl acetate (50% solution) was added at a time and refluxed with heat over 12 hours. The reaction mixture was condensed under reduced pressure. A N-propionylethyleneimine-dimethylsiloxane copolymer was obtained as a pale yellow rubber-like solid (468 g; yield=97%). The %content of silicone segments was 61%, and the weight-average molecular weight was 102,000. When a neutralization titration was performed using HCl in methanol, no residual amino groups were found.

Synthesis Example 7

Organopolysiloxane A-6:

Diethyl sulfate (3.75 g; 0.0243 mol) and 2-ethyl-2-oxazoline (49.8 g; 0.585 mol) were dissolved in dehydrated ethyl acetate (107 g). The solution was refluxed with heat for 5 hours in an atmosphere of nitrogen to synthesize a terminal reactive poly(N-acetylethyleneimine). To this, a side-chain primary aminopropyl-modified polydimethylsiloxane (molecular weight: 110,000, amine equivalent: 9840) (400 g; amino group equivalent=0.0407 mol) in ethyl acetate (50% solution) was added at a time and refluxed with heat over 13 hours. The reaction mixture was condensed under reduced pressure. A N-acetylethyleneimine-dimethylsiloxane copolymer was obtained as a pale yellow rubber-like solid (444 g; yield=98%). The % content of silicone segments was 88%, and the weight-average molecular weight was 137,000. When a neutralization titration was performed using HCl in methanol, no residual amino groups were found.

Synthesis Example 8

Organopolysiloxane C-1:

Gamma-aminopropyl-modified dimethylpolysiloxane (200 g; 0.493 mol as converted to amino groups) which has an amine equivalent of 406 and a weight-average molecular weight of 36,000, maltobionolactone (201 g; 0.591 mol) and ethanol (800 g) were mixed. The mixture was refluxed with heat for 9 hours under vigorous agitation in an atmosphere of nitrogen. The resultant solution was vigorously agitated at room temperature, to which hexane (1000 g) was added. The sedimented pellet was removed by filtration, and the filtrate was condensed under reduced pressure. Dimethylpolysiloxane containing a saccharide residue was obtained as a colorless transparent elastic solid (342 g; yield=93%). When a neutralization titration was performed using HCl in methanol, no residual amino groups were found. The % content of silicone segments was 54%.

Synthesis Example 9

Organopolysiloxane C-2:

Gamma-aminopropyl-modified dimethylpolysiloxane (200 g; 0.201 mol as converted to amino groups) which has an amine equivalent of 996 and a weight-average molecular weight of 108,000, delta-glucolactone (39.3 g; 0.221 mol) and methanol (200 g) were mixed. The mixture was refluxed with heat for 8 hours under vigorous agitation in an atmosphere of nitrogen. The resultant solution was diluted in three fold with methanol, and was added to water (10 l) dropwise under vigorous agitation. Subsequently, agitation was stopped, and a pellet was collected by filtration. It was washed with water and then dried under reduced pressure. As a result, dimethylpolysiloxane containing saccharide residues was obtained as a colorless transparent elastic solid (204 g; yield=86%). When a neutralization titration was performed using HCl in methanol, no residual amino groups were found. The % content of silicone segments was 86%.

Synthesis Example 10

Organopolysiloxane C-3:

Gamma-aminopropyl-modified dimethylpolysiloxane (200 g; 0.0201 mol as converted to amino groups) which has an amine equivalent of 9,940 and a weight-average molecular weight of 128,000, maltobionolactone (8.22 g; 0.0241 mol) and ethanol (300 g) were mixed. The mixture was refluxed with heat for 9 hours under vigorous agitation in an atmosphere of nitrogen. The resultant solution was diluted in 2.5 fold with ethanol, and was added to water (10 l) dropwise under vigorous agitation. Subsequently, agitation was stopped, and pellet was collected by filtration. It was washed with water and then dried under reduced pressure. As a result, a dimethylpolysiloxane containing saccharide residues was obtained as a colorless transparent elastic solid (206 g; yield=92%). When a neutralization titration was performed using HCl in methanol, no residual amino groups were found. The % content of silicone segments was 97%.

Comparative Synthesis Example 3

Organopolysiloxane c containing a saccharide residue was prepared by the following method.

A mixture of 50 g (0.0694 mol by a primary amino group conversion) of 6-amino-4-azahexyl-modified dimethylpolysiloxane (product of Shin'estu Kagaku Kogyo, KF393) having an amine equivalent of 360 and a weight-average molecular weight of 3,800, 13 g of glucono-delta-lactone and 200 ml of methanol was refluxed for 6 hours. Methanol was distilled off under reduced pressure. The residue was dissolved in water. An aqueous solution of the reaction mixture was placed in a transparent cellophane tube, and dialyzed to remove gluconic acid originated from unreacted glucono-delta-lactone. The resultant material was freeze-dried, to obtain 60 g of 6-gluconamide-4-azahexyl-modified organopolysiloxane c as a white solid (yield: 95%). When a neutralization titration was performed using HCl in methanol, no residual amino groups were found. The % content of silicone segments was 70%.

Synthesis Example 11

Organopolysiloxane D-1:

Diethyl sulfate (30.6 g; 0.198 mol) and 1-(2-carboethoxyethyl)azetidine (1498.2 g; 9.53 mol) were dissolved in dehydrated ethyl acetate (3058 g), and refluxed with heat for 15 hours in an atmosphere of nitrogen to synthesize a terminal reactive poly(N-propylene imine). To this, a side-chain primary aminopropyl-modified polydimethylsiloxane (molecular weight: 110,000, amine equivalent: 4840) (800 g; amino group equivalent=0.165 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (2212 g; yield=95%). The resultant reaction product was dispersed in methanol (5000 g), to which sodium chloroacetate (1665.6 g; 14.3 mol) was added. The mixture was allowed to react for 24 hours while refluxing with heat. The reaction solution was cooled to room temperature, and sodium chloride was filtered off. The obtained solution was condensed under reduced pressure to obtain an N-propylene carbobetaine-dimethylsiloxane copolymer as a pale yellow solid.

Synthesis Example 12

Organopolysiloxane D-2:

Diethyl sulfate (3.56 g; 0.023 mol) and 1-(2-carboethoxyethyl)azetidine (43.5 g; 0.277 mol) were dissolved in dehydrated ethyl acetate (94.2 g), and refluxed with heat for 6 hours in an atmosphere of nitrogen to synthesize a terminal reactive poly(N-propylene imine). To this, a side-chain primary aminopropyl-modified polydimethylsiloxane (molecular weight: 110,000, amine equivalent: 20800) (400 g; amino group equivalent=0.0192 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (425 g; yield=95%). The resultant reaction product was dispersed in methanol (1000 g), to which sodium chloroacetate (46.6 g; 0.4 mol) was added. The mixture was allowed to react for 24 hours while refluxing with heat. The reaction solution was cooled to room temperature, and sodium chloride was filtered off. The obtained solution was condensed under reduced pressure to obtain an N-propylene carbobetaine-dimethylsiloxane copolymer as a pale yellow solid.

Synthesis Example 13

Organopolysiloxane D-3:

Diethyl sulfate (30.6 g; 0.198 mol) and 1-(2-carboethoxyethyl)azetidine (1498.2 g; 9.53 mol) were dissolved in dehydrated ethyl acetate (3058 g), and refluxed with heat for 15 hours in an atmosphere of nitrogen to synthesize a terminal reactive poly(N-propylene imine). To this, a side-chain primary aminopropyl-modified polydimethylsiloxane (molecular weight: 110,000, amine equivalent: 4840) (800 g; amino group equivalent=0.165 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (2212 g; yield=95%). The resultant reaction product was dispersed in diethylether (5000 g), to which β-propiolactone (824 g; 11.4 mol) was added at room temperature. The mixture was allowed to react for a day and night at room temperature. The obtained mixture was condensed under reduced pressure to obtain an N-propylene carbobetaine-dimethylsiloxane copolymer as a pale yellow solid.

Synthesis Example 14

Organopolysiloxane D-4:

Diethyl sulfate (3.56 g; 0.023 mol) and 1-(2-carboethoxyethyl)azetidine (43.5 g; 0.277 mol) were dissolved in dehydrated ethyl acetate (94.2 g), and refluxed with heat for 6 hours in an atmosphere of nitrogen to synthesize a terminal reactive poly(N-propylene imine). To this, a side-chain primary aminopropyl-modified polydimethylsiloxane (molecular weight: 110,000, amine equivalent: 20800) (400 g; amino group equivalent=0.0192 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (425 g; yield=95%). The resultant reaction mixture was dissolved in diethylether (1000 g), to which β-propiolactone (23.95 g; 0.332 mol) was added at room temperature. The mixture was allowed to react for a day and night at room temperature. The obtained mixture was condensed under reduced pressure to obtain an N-propylene carbobetaine-dimethylsiloxane copolymer as a pale yellow solid.

Synthesis Example 15

Organopolysiloxane D-5:

Triethyloxonium tetrafluoroborate (37.6 g; 0.198 mol) and 1-(2-carboethoxyethyl)azetidine (1498.2 g; 9.53 mol) were dissolved in dehydrated tetrahydrofuran (3058 g), and refluxed with heat for 15 hours in an atmosphere of nitrogen to synthesize a terminal reactive poly(N-propylene imine). To this, a side-chain primary aminopropyl-modified polydimethylsiloxane (molecular weight: 110,000, amine equivalent: 4840) (800 g; amino group equivalent=0.165 mol) in tetrahydrofuran (50% solution) was added at a time and refluxed with heat over 12 hours. The reaction mixture was condensed under reduced pressure. A N-propyleneimine-dimethylsiloxane copolymer was obtained as a pale yellow solid (2212 g; yield=95%). The obtained reaction mixture was dissolved in diethylether (5000 g), to which γ-butyrolactone (981.4 g; 11.4 mol) was added at room temperature. The mixture was allowed to react for a day and night at room temperature. The obtained solution was condensed under reduced pressure to obtain an N-propylene carbobetaine-dimethylsiloxane copolymer as a pale yellow solid.

Synthesis Example 16

Organopolysiloxane D-6:

Trifluoromethanesulfonic acid (3.45 g; 0.023 mol) and 1-(2-carboethoxyethyl)azetidine (43.5 g; 0.277 mol) were dissolved in dehydrated diisopropyl ether (94.2 g), and refluxed with heat for 6 hours in an atmosphere of nitrogen to synthesize a terminal reactive poly(N-propylene imine). To this, a side-chain primary aminopropyl-modified polydimethylsiloxane (molecular weight: 110,000, amine equivalent: 20800) (400 g; amino group equivalent=0.0192 mol) in diisopropyl ether (50% solution) was added at a time and refluxed with heat over 12 hours. The reaction mixture was condensed under reduced pressure. A N-propyleneimine-dimethylsiloxane copolymer was obtained as a pale yellow solid (425 g; yield=95%). The resultant reaction mixture was dissolved in diethylether (1000 g), to which ε-caprolactone (37.9 g; 0.332 mol) was added at room temperature. The mixture was allowed to react for a day and night at room temperature. The obtained mixture was condensed under reduced pressure to obtain an N-propylene carbobetaine-dimethylsiloxane copolymer as a pale yellow solid.

Synthesis Example 17

Organopolysiloxane D-7:

Diethyl sulfate (30.6 g; 0.198 mol) and 1-(2-carboethoxyethyl)azetidine (1498.2 g; 9.53 mol) were dissolved in dehydrated ethyl acetate (3058 g), and refluxed with heat for 15 hours in an atmosphere of nitrogen to synthesize a terminal reactive poly(N-propylene imine). To this, a side-chain primary aminopropyl-modified polydimethylsiloxane (molecular weight: 110,000, amine equivalent: 4840) (800 g; amino group equivalent=0.165 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (2212 g; yield=95%). The resultant reaction mixture was dissolved in acetone (5000 g), to which ethyl bromide (1246.2 g; 11.44 mol) was added. The mixture was allowed to react for 24 hours while refluxing with heat. The reaction mixture was condensed under reduced pressure, and dispersed in methanol (5000 g). 2N potassium hydroxide in methanol (5000 g) was added thereto, and then heated at 80° C. for 6 hours. The obtained solution was condensed under reduced pressure, dissolved in chloroform, washed with water, and condensed under reduced pressure again to obtain an N-propylene carbobetaine-dimethylsiloxane copolymer as a pale yellow solid.

Synthesis Example 18

Organopolysiloxane D-8:

Diethyl sulfate (3.56 g; 0.023 mol) and 1-(2-carboethoxyethyl)azetidine (43.5 g; 0.277 mol) were dissolved in dehydrated ethyl acetate (94.2 g), and refluxed with heat for 6 hours in an atmosphere of nitrogen to synthesize a terminal reactive poly(N-propylene imine). To this, a side-chain primary aminopropyl-modified polydimethylsiloxane (molecular weight: 110,000, amine equivalent: 20800) (400 g; amino group equivalent=0.0192 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (425 g; yield=95%). The resultant reaction product was dissolved in acetone (1000 g), to which ethyl bromide (25.2 g; 0.231 mol) was added. The mixture was allowed to react for 24 hours while refluxing with heat. The reaction mixture was condensed under reduced pressure, and dispersed in methanol (1000 g). 2N potassium hydroxide in methanol (150 g) was added thereto, and then heated at 80° C. for 6 hours. The obtained solution was condensed under reduced pressure, dissolved in chloroform, washed with water, and condensed under reduced pressure again to obtain an N-propylene carbobetaine-dimethylsiloxane copolymer as a pale yellow solid.

Synthesis Example 19

Organopolysiloxane D-9:

Diethyl sulfate (30.6 g; 0.198 mol) and 1-(2-carboethoxyethyl)azetidine (1498.2 g; 9.53 mol) were dissolved in dehydrated ethyl acetate (3058 g), and refluxed with heat for 15 hours in an atmosphere of nitrogen to synthesize a terminal reactive poly(N-propylene imine). To this, a side-chain primary aminopropyl-modified polydimethylsiloxane (molecular weight: 110,000, amine equivalent: 4840) (800 g; amino group equivalent=0.165 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (2212 g; yield=95%). The resultant reaction mixture was dissolved in acetone (5000 g), to which hexyl bromide (1888.5 g; 11.44 mol) was added. The mixture was allowed to react for 24 hours while refluxing with heat. The reaction mixture was condensed under reduced pressure, and dispersed in methanol (5000 g). 2N potassium hydroxide in methanol (5000 g) was added thereto, and then heated at 80° C. for 6 hours. The obtained solution was condensed under reduced pressure, dissolved in chloroform, washed with water, and condensed under reduced pressure again to obtain an N-propylene carbobetaine-dimethylsiloxane copolymer as a pale yellow solid.

Synthesis Example 20

Organopolysiloxane D-10:

Diethyl sulfate (3.56 g; 0.023 mol) and 1-(2-carboethoxyethyl)azetidine (43.5 g; 0.277 mol) were dissolved in dehydrated ethyl acetate (94.2 g), and refluxed with heat for 6 hours in an atmosphere of nitrogen to synthesize a terminal reactive poly(N-propylene imine). To this, a side-chain primary aminopropyl-modified polydimethylsiloxane (molecular weight: 110,000, amine equivalent: 20800) (400 g; amino group equivalent=0.192 mol) in ethyl acetate (50% solution) was added at a time and refluxed with heat over 12 hours. The reaction mixture was condensed under reduced pressure. A N-propyleneimine-dimethylsiloxane copolymer was obtained as a pale yellow solid (425 g; yield=95%). The resultant reaction mixture was dissolved in acetone (1000 g), to which hexyl bromide (38.1 g; 0.231 mol) was added. The mixture was allowed to react for 24 hours while refluxing with heat. The reaction mixture was condensed under reduced pressure, and dispersed in methanol (1000 g). 2N potassium hydroxide in methanol (150 g) was added thereto, and then heated at 80° C. for 6 hours. The obtained solution was condensed under reduced pressure, dissolved in chloroform, washed with water, and condensed under reduced pressure again to obtain an N-propylene carbobetaine-dimethylsiloxane copolymer as a pale yellow solid.

Reference Example 1

The organopolysiloxanes according to the present invention which were obtained in Synthesis Examples 1 to 20, low-molecular weight organopolysiloxanes obtained in Comparative Synthesis Examples 1 to 3, and the below-described commercially obtained set polymers d and e were evaluated in terms of the film-forming property in the method described below. The results follow the description of the method.

d: Yukaformer M-75 (by Mitsubishi Petrochemical)

e: Gantrez ES 225 (by GAF)

Evaluation Method

Each polymer was made into a 10% ethanol solution. Ethanol was spontaneously evaporated to form a film having a thickness of about 0.2 to 0.3 mm. A sample having a length of 20 mm and a width of 5 mm was cut out from this film. The sample was attached to a tension meter placed in a room of 65% relative humidity. The stress-strain curve was recorded, during which the sample was stretched by 3 mm at a cross head speed of 20 mm/min. Immediately thereafter, the cross head was returned to its original position at the same speed. After ten minutes, the sample was stretched again, and the stress-strain curve was recorded.

Results

When the organopolysiloxanes according to present invention were stretched, the stress-strain curves of the first and the second times were identical. This means that no plastic deformation was caused by the first stretching. By contrast, when the commercially obtained set polymer d was stretched, it ruptured at the first stretching. In the cases of the organopolysiloxanes and c obtained in Comparative Synthesis Examples 1 and 3, respectively, and the commercially obtained set polymer e, the second stress-strain curve was not identical to the first curve, which indicates that plastic deformation was caused by the first stretching. When the films formed with the organopolysiloxanes according to the present invention were observed under transmission electron microscope (TEM), it was found that all of them were cross-linked and had a micro phase separation structure.

Reference Example 2

The solubility of the organopolysiloxanes according to present invention obtained in Synthesis Examples 1 to 20 was determined in ethanol and in an aqueous 20% ethanol solution. In both cases, the compounds were either uniformly dissolved to form a transparent solution or uniformly dispersed to form a translucent dispersion at a concentration of 2 wt %. By contrast, room temperature-setting type Silicone Elastomer SH 9585 (by Shin'etsu Kagaku Kogyo) and Silicone Elastomer KE-10 (covalent bond cross-linking type) were neither dissolved nor dispersed at the same concentration. Examples 1 to 6 and Comparative Examples 1 to 5:

The organopolysiloxanes according to the present invention which were obtained in Synthetic Examples 1 to 5, the organopolysiloxanes a–c obtained in Comparative Synthesis Examples 1–3, and the above-mentioned commercially obtained polymers d and e were used to prepare hair set mists formulated as shown in Table 1. Hair fibers were treated with the obtained mists, and were tested with regard to the evaluation items described below. The results are also shown in Table 1.

(a) Set retentivity

A hair tress (18 cm, 1.5 g) was wet with water, and then towel-dried. Mist (2 g) was applied thereto and wound on a rod having a diameter of 2 cm, then spontaneously dried. After being dried, the curled hair was removed from the rod, and suspended in a highly humid chamber (20° C., 98%RH) for 30 minutes. The shape of the curl was observed. The set retentivity was determined based on the following:

Evaluation Standard:

A: Very much superior to untreated hair

B: Superior to untreated hair

C: Comparable to untreated hair

D: Inferior to untreated hair (b) Sensory Evaluation

A hair tress (18 cm, 10 g) was wet with water, and then towel-dried. Mist (2 g) was applied thereto and wound on a rod having a diameter of 2 cm, then spontaneously dried. Five expert panelists evaluated the touch to the hair.

Evaluation Standard:

A: Very much superior to untreated hair

B: Superior to untreated hair

C: Comparable to untreated hair

D: Inferior to untreated hair

E: Very much inferior to untreated hair (c) Elasticity of curls

Curls were formed by a similar method described in (a) above. Five expert panelists evaluated the elasticity of curls.

Evaluation Standard:

A: More elastic than untreated hair

B: Slightly more elastic than untreated hair

C: Comparable to untreated hair

D: Stiff and rough compared to untreated hair

TABLE 1

(wt. %)

| Components/ Evaluation | Test Examples |||||||||||
|---|---|---|---|---|---|---|---|---|---|---|---|
| | Products of Present Invention |||||| Comparative Examples |||||
| | 1 | 2 | 3 | 4 | 5 | 6 | 1 | 2 | 3 | 4 | 5 |
| Organopolysiloxane A-1 | 2.0 | — | — | — | — | — | — | — | — | — | — |
| Organopolysiloxane A-2 | — | 2.0 | — | — | — | — | — | — | — | — | — |
| Organopolysiloxane A-3 | — | — | 2.0 | — | — | — | — | — | — | — | — |
| Organopolysiloxane B-1 | — | — | — | 2.0 | — | — | — | — | — | — | — |
| Organopolysiloxane C-1 | — | — | — | — | 2.0 | — | — | — | — | — | — |
| Organopolysiloxane D-1 | — | — | — | — | — | 2.0 | — | — | — | — | — |
| Organopolysiloxane a | — | — | — | — | — | — | 2.0 | — | — | — | — |
| Organopolysiloxane b | — | — | — | — | — | — | — | 2.0 | — | — | — |
| Organopolysiloxane c | — | — | — | — | — | — | — | — | 2.0 | — | — |
| Commercially available polymer d | — | — | — | — | — | — | — | — | — | 2.0 | — |
| Commercially available polymer e | — | — | — | — | — | — | — | — | — | — | 2.0 |
| Perfume | | | | | | trace | | | | | |
| Ethanol | | | | | | balance | | | | | |
| Total | 100.0 | 100.0 | 100.0 | 100.0 | 100.0 | 100.0 | 100.0 | 100.0 | 100.0 | 100.0 | 100.0 |
| (a) Set retentivity | A | A | B | A | A | A | C | C | C | A | B |
| (b) Sensory evaluation | A | A | A | A | A | A | A | A | A | E | D |
| (c) Elasticity of curls | A | B | A | A | A | A | C | C | C | D | D |

As shown in Table 1, the products according to the present invention are all superior to the comparative products in terms of the set retentivity, touch to the hair and elasticity of curls. In addition, the products according to the present invention exhibited excellent removal-by-shampoo property. Although not shown in Table 1, the organopolysiloxanes according to the present invention obtained in Synthesis Examples 5 to 7, 9, 10 and 12 to 20 also exhibit excellent set retentivity, and touch to the hair, and the curls had elasticity.

Example 7

Organopolysiloxanes according to the present invention and a film-forming polymer were used, and the mists shown in Table 2 were prepared.

The mists were applied to the hair, and were evaluated with regard to the set retentivity and smoothness of the hair by testing them as described below. Evaluation was made based on the following criteria. The results are also shown in Table 2.

(a) Set retentivity

A hair tress (18 cm, 1.5 g) was wet with water, and then towel-dried. Mist (2 g) was applied thereto and wound on a rod having a diameter of 2 cm, then spontaneously dried. After being dried, the curled hair was removed from the rod, and suspended in a thermostat chamber (20° C., 98%RH) for 30 minutes. The shape of the curl was observed. The set retentivity was determined based on the following criteria:

Evaluation Standard:

A: Excellent

B: Good

C: Ordinary

D: Slightly poor

E: Poor (b) Smoothness

A hair tress (18 cm, 10 g) was wet with water, and then towel-dried. Mist (0.2 g) was applied thereto and then spontaneously dried. Smoothness of the hair was evaluated based on the following criteria:

Evaluation Standard:

A: Excellent

B: Good

C: Ordinary

D: Slightly poor

E: Poor

TABLE 2

(wt. %)

| Components Evaluation | Mists |||||||||||
|---|---|---|---|---|---|---|---|---|---|---|---|
| | Products of Present Invention |||||| Comparative Products |||||
| | A | B | C | D | E | F | G | H | I | J | K |
| Organopolysiloxane C-1 | 1.5 | — | — | — | — | — | — | — | — | — | — |
| Organopolysiloxane C-2 | — | 1.5 | — | — | — | — | — | — | — | — | — |
| Organopolysiloxane C-3 | — | — | 0.5 | — | — | — | — | — | — | — | — |
| Organopolysiloxane A-6 | — | — | — | 1.0 | — | — | — | — | 1.0 | — | — |
| Organopolysiloxane B-1 | — | — | — | — | 1.5 | — | — | — | — | 1.5 | — |
| Organopoiysiloxane D-2 | — | — | — | — | — | 0.5 | — | — | — | — | 1.5 |
| Amphoteric polymer (Yukaformer M-75, by Mitsubishi Petrochemical) | 0.5 | 0.5 | 1.5 | 1.0 | 0.5 | 1.5 | 2.0 | 0.5 | 1.0 | 0.5 | 0.5 |

TABLE 2-continued

| | | | | | | | | | | | (wt. %) |
|---|---|---|---|---|---|---|---|---|---|---|---|
| | Mists | | | | | | | | | | |
| Components | Products of Present Invention | | | | | | Comparative Products | | | | |
| Evaluation | A | B | C | D | E | F | G | H | I | J | K |
| Perfume | | | | | trace | | | | | | |
| Ethanol | | | | | balance | | | | | | |
| Total | 100.0 | 100.0 | 100.0 | 100.0 | 100.0 | 100.0 | 100.0 | 100.0 | 100.0 | 100.0 | 100.0 |
| Set retentivity | A | A | A | A | A | A | A | D | D | E | D |
| Smoothness | B | A | A | A | A | A | E | D | C | B | B |

As shown in Table 2, the products according to the present invention are all superior to the comparative products in terms of the set retentivity and smoothness of the hair. Although not shown in Table 2, the compositions containing the organopolysiloxanes obtained in Synthesis Examples 1–3, 5, 6, 11 and 13–20 and an amphoteric polymer also exhibit excellent set retentivity, and impart excellent smoothness to the hair after treatment.

The comparative products I, J and K, which contain an organopolysiloxane which does not meet the requirements of the present invention, have poor set retentivity, though they exhibit good performance with regard to the smoothness of the set hair.

Example 8

A foam agent was prepared by blending the following components.

| (Components) | (wt. %) |
|---|---|
| Organopolysiloxane A-1 | 3.0 |
| Coconut oil fatty acid diethanolamide | 0.5 |
| Ethanol | 20.0 |
| Perfume | trace |
| Purified water | balance |
| Liquefied petroleum gas | 10.0 |
| Total | 100.0 |

Example 9

A foam agent was prepared by blending the following components.

| (Components) | (wt. %) |
|---|---|
| Organopolysiloxane A-3 | 1.0 |
| Commercially available setting polymer (GANTREZ ES 225, product of GAF) | 2.0 |
| Cetyltrimethyl ammonium chloride solution (25%) | 0.5 |
| Ethanol | 15.0 |
| Perfume | trace |
| Purified water | balance |
| Liquefied petroleum gas | 10.0 |
| Total | 100.0 |

The foam agents obtained in Examples 8 and 9 all exhibit excellent set retentivity and favorable touch to the hair and the curls have elasticity.

Example 10

A mist agent was prepared by blending the following components.

| (Components) | (wt. %) |
|---|---|
| Organopolysiloxane A-1 | 2.0 |
| Ethanol | 30.0 |
| Perfume | trace |
| Purified water | balance |
| Total | 100.0 |

Example 11

A hair set lotion was prepared by blending the following components.

| (Components) | (wt. %) |
|---|---|
| Organopolysiloxane A-1 | 1.0 |
| Ethanol | balance |
| Perfume | trace |
| Purified water | 10.0 |
| Total | 100.0 |

Example 12

A hair spray was prepared by blending the following components.

| (components) | (wt. %) |
|---|---|
| Organopolysiloxane B-1 | 5.0 |
| Ethanol | balance |
| Perfume | trace |
| Liquefied petroleum gas | 50.0 |
| Total | 100.0 |

The hair cosmetic compositions obtained in Examples 8 to 10 exhibit excellent set retentivity and favorable touch to the hair, and the curls have elasticity. In addition, the removal-by-shampoo property was not impeded.

Example 13

A blow agent containing the following components was prepared in accordance with a conventional method.

| (Components) | (wt. %) |
| --- | --- |
| Organopolysiloxane C-1 | 0.5 |
| Amphoteric polymer (Yukaformer M-75) | 0.5 |
| Perfume | trace |
| Ethanol | 30.0 |
| Purified water | suitable amount |
| Total | 100.0 |

Example 14

A foam agent containing the following components was prepared in accordance with a conventional method.

| (Components) | (wt. %) |
| --- | --- |
| Organopolysiloxane C-1 | 1.0 |
| Chitin liquid (product of Ichimaru-Pharcos) | 5.0 |
| Nonionic surfactant (Softanol 90, product of Nihon Shokubai) | 1.0 |
| Perfume | trace |
| Purified water | balance |
| Liquefied petroleum gas | 10.0 |
| Total | 100.0 |

Example 15

A hair spray containing the following components was prepared in accordance with a conventional method.

| (Components) | (wt. %) |
| --- | --- |
| Organopolysiloxane C-3 | 1.5 |
| Nonionic polyiner (Luviskol VA37, product of BASF) | 5.0 |
| Perfume | trace |
| Ethanol | balance |
| Liquefied petroleum gas | 50.0 |
| Total | 100.0 |

Example 16

A hair set lotion containing the following components was prepared in accordance with an ordinary manner.

| (Components) | (wt. %) |
| --- | --- |
| Organopolysiloxane C-2 | 1.0 |
| Amphoteric polymer (Yukaformer M-75) | 2.0 |
| Ethanol | balance |
| Purified water | 10.0 |
| Perfume | trace |
| Total | 100.0 |

The hair setting agents obtained in Examples 13 to 16 are all excellent in terms of set retentivity, smoothness, natural gloss, softness, elasticity, easy combing and water repellency.

Example 17

A foam agent was obtained by blending the following components.

| (Components) | (wt. %) |
| --- | --- |
| Organopolysiloxane D-1 | 3.0 |
| Polyoxyethylene (9) tetradecyl ether | 0.5 |
| Ethanol | 10.0 |
| Perfume | 0.10 |
| Liquefied petroleum gas | 10.0 |
| Purified water | balance |
| Total | 100.0 |

Example 18

A hair spray was obtained by blending the following components.

| (Components) | (wt. %) |
| --- | --- |
| Organopolysiloxane D-5 | 3.0 |
| Squalane | 0.1 |
| Methylphenyl polysiloxane (KF-53 by Shin'etsu) | 0.15 |
| Perfume | 0.10 |
| Liquefied petroleum gas | 25.0 |
| Dimethylether | 25.0 |
| Ethanol | balance |
| Total | 100.0 |

Example 19

A foam agent was obtained by blending the following components.

| (Components) | (wt. %) |
| --- | --- |
| Organopolysiloxane D-8 | 1.0 |
| Anionic polymer (Gantrey ES 225 by GAF) | 1.5 |
| Polyoxyethylene (9) tetradecyl ether | 0.5 |
| Ethanol | 10.0 |
| Perfume | 0.10 |
| Liquefied petroleum gas | 10.0 |
| Purified water | balance |
| Total | 100.0 |

The hair setting agents obtained in Examples 17–19 all exhibited excellent set retentivity and favorable touch to the hair and the curls had elasticity.

Example 20

A foam agent was prepared by blending the following components.

| (Components) | (wt. %) |
| --- | --- |
| Organopolysiloxane A-2 | 2.70 |
| Salf of Chitosan (Chitomer PC, product of Union Carbide) | 0.30 |
| Ethanol | 15.0 |
| Coconut oil fathy acid diethanolamide | 0.4 |
| Cationic polymer | 0.1 |

-continued

| (Components) | (wt. %) |
| --- | --- |
| (Polymer JR400, product of Union Carbide) | |
| Perfume | trace |
| Purified water | balance |
| Liquefied petroleum gas | 10.0 |
| | 100.0 |

The foam agent obtained in Examples 20 exhibited excellent set retentivity and favorable touch to the hair and curls had elasticity.

Example 21

A blow agent containing the following components was prepared in accordance with a conventional method.

| (Components) | (wt. %) |
| --- | --- |
| Organopolysiloxane A-2 | 2.0 |
| Dimethylpolysiloxane emulsion | 1.0 |
| (L-13, product of Toray Dow Corning Silicone) | |
| Cetyltrimethyl ammonium chloride | 0.1 |
| Ethanol | 20.0 |
| Perfume | trace |
| Purified water | balance |
| | 100.0 |

The blow agent obtained in Example 21 exhibited excellent blow setting effect and soft and smooth touch to the hair.

We claim:

1. A method of setting hair comprising the steps of:

applying, to hair, a composition containing an organopolysiloxane which is capable of intramolecular or dipole-dipole interaction, hydrogen bonding or ion bonding, and which is not ruptured or plastically deformed at an extension ratio no more than 15% at a temperature of 20° C. under relative humidity of 65%; and removing, any solvent present in the composition, wherein in said organopolysiloxane at least one silicon atom in a side chain or at a terminal of an organopolysiloxane segment is bonded, through an alkylene group having a hetero atom, to poly(N-acylalkyleneimine) constituted by recurring units in a polymer chain represented by the following formula (1):

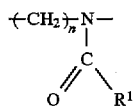

wherein $R^1$ represents hydrogen, $C_1$–$C_{22}$ alkyl, cycloalkyl, aralkyl or aryl, and n represents a number of 2 or 3, and wherein the ratio by weight between the organopolysiloxane segment and the poly(N-alkyleneimine) segment is from 98/2 to 40/60, and the weight-average molecular weight of the organopolysiloxane is from 50,000 to 500,000.

2. A method for setting hair according to claim 1, wherein said composition further comprises a film-forming polymer.

3. A method of setting hair according to claim 1, wherein the removal of the solvent is carried out at room temperature or higher.

* * * * *